United States Patent
Lee

(10) Patent No.: US 6,766,269 B2
(45) Date of Patent: Jul. 20, 2004

(54) LPG FUEL COMPOSITION ESTIMATION METHOD AND SYSTEM

(75) Inventor: Woo-Jik Lee, Suwon (KR)

(73) Assignee: Hyundai Motor Company, Seoul (KR)

( * ) Notice: Subject to any disclaimer, the term of this patent is extended or adjusted under 35 U.S.C. 154(b) by 0 days.

(21) Appl. No.: 10/331,226

(22) Filed: Dec. 30, 2002

(65) Prior Publication Data

US 2003/0216883 A1 Nov. 20, 2003

(30) Foreign Application Priority Data

May 20, 2002 (KR) .................................. 10-2002-27803

(51) Int. Cl.[7] .............................................. G06F 19/00
(52) U.S. Cl. .................. 702/136; 702/50; 123/526; 123/527; 73/204
(58) Field of Search ................... 73/204.11, 20, 73/4.22, 204.24, 204; 123/526, 527, 478, 301, 27 GE; 702/136

(56) References Cited

U.S. PATENT DOCUMENTS 5,379,740 A * 1/1995 Moore et al. ............... 123/478
6,389,874 B1 * 5/2002 Huff et al. .................... 73/1.02
6,629,455 B2 * 10/2003 Schrittenlacher et al. 73/204.22

* cited by examiner

Primary Examiner—Kamini Shah
(74) Attorney, Agent, or Firm—Morgan Lewis & Bockius LLP

(57) ABSTRACT

A Liquefied Petroleum Gas (LPG) fuel composition estimation method is provided that determines an LPG fuel composition from saturation vapor pressure data and an estimated fuel temperature and fuel pressure inside the fuel tank. A Liquefied Petroleum Gas Injection (LPI) System that employs the method is provided that employs the method of the invention.

11 Claims, 5 Drawing Sheets

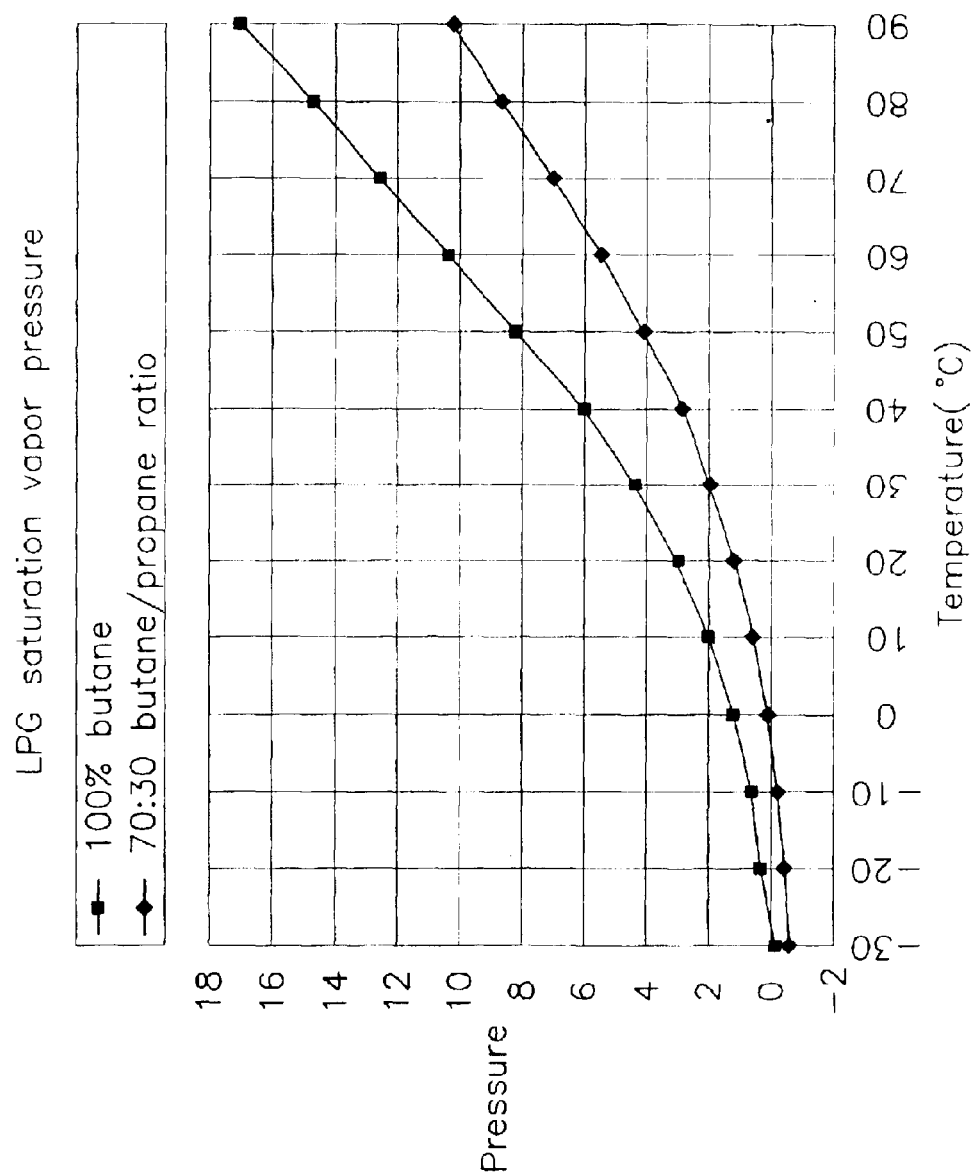

LPG FUEL COMPOSITION ESTIMATION METHOD AND SYSTEM

FIELD OF THE INVENTION

The present invention relates to an LPG (Liquefied Petroleum Gas) fuel system for a vehicle. More particularly, the invention relates to a method and a system for determining the fuel pressure and the fuel temperature inside the fuel tank of the LPG fuel system, and for estimating the LPG fuel composition based on the determined fuel pressure and fuel temperature.

BACKGROUND OF THE INVENTION

Generally, an LPI (LPG injection) system used for supplying fuel to a combustion chamber includes a fuel pump that is disposed in a fuel tank that stores LPG fuel. The LPG fuel is pressurized by the fuel pump so that it is in a liquid state in the fuel supply line. The pressurized liquid fuel is injected by an injector into the combustion chamber.

Because it is more difficult to meter the LPG fuel into injectors when the LPG fuel is in a gaseous state, it is desirable to maintain the LPG fuel in the liquid state. And fuel injection control in the LPG vehicle is generally performed based on the assumption that the LPG fuel is in a liquid state.

When liquid LPG fuel vaporizes, the volume of the fuel increases by about 250 times. Therefore, if the liquid LPG fuel vaporizes during fuel injection, the amount of fuel injected into a combustion chamber is substantially decreased. To deliver the LPG fuel in the liquid state, the LPG fuel stored in the fuel tank is pressurized by the fuel pump and delivered to the injector.

In a conventional LPG vehicle, without the fuel pump, where the gaseous LPG fuel is delivered to the engine by the fuel vapor pressure itself, the lower the temperature of the LPG fuel, the less the amount of LPG fuel supplied to the combustion chamber. This causes startability and acceleration problems.

LPG is a petroleum-derived colorless gas, typically comprised primarily of either propane, a butane, or a combination of the two. LPG has been the most widely used alternative motor fuel to gasoline and diesel thus far. The butane/propane ratio of the LPG fuel is varied according to environmental situations, such as temperature. For example, it is preferable that the fuel contains 100% butane during hot summer, when the LPG fuel may be more easily evaporated because butane has a higher vaporization point. On the other hand, the butane/propane ratio of the LPG fuel is preferably 70:30 during cold winter. That is, it is preferable that the ratio of the propane is increased with a temperature decrease.

In an LPI engine that uses only LPG fuel, the amount of fuel injected and the ignition timing are determined on the basis of the liquid state of the LPG fuel when the LPG fuel tank is filled. Therefore, when liquid LPG fuel and gaseous LPG fuel coexist in the same tank, it is impossible to optimally control the fuel injection. Thus, it is desirable to determine whether the LPG fuel is in a liquid state. To determine whether the LPG fuel is in a liquid state, the LPG fuel composition must be known, that is, the butane/propane ratio of the LPG fuel must be determined.

The butane/propane ratio of the LPG fuel can be determined based on the temperature and pressure of the LPG fuel inside the fuel tank and saturation vapor pressure data. These are easily acquired by utilizing sensors detecting the temperature and the pressure of the fuel inside the fuel tank. But it is difficult to install sensors for detecting the temperature and the pressure of the LPG fuel inside the fuel tank, and furthermore, such sensors increase the cost of the fuel system.

SUMMARY OF THE INVENTION

In a preferred embodiment of the present invention, the LPG (Liquefied Petroleum Gas) fuel composition estimation method for an LPI (LPG Injection) system comprises: detecting a fuel pressure inside a fuel supply line, a fuel temperature inside the fuel supply line, a coolant temperature, and an intake air temperature at an ignition-on state; determining whether differences between the detected temperatures fall within predetermined conditions; detecting the fuel temperature and the fuel pressure inside the fuel supply line at intervals; determining a fuel temperature and a fuel pressure inside a fuel tank based on the detected fuel temperature and fuel pressure inside the fuel supply line, if it is determined that the predetermined conditions exist; and determining an LPG fuel composition from saturation vapor pressure data based on the determined fuel temperature and fuel pressure inside the fuel tank.

Preferably, the predetermined conditions comprise: a temperature difference between the fuel temperature inside the fuel supply line and the coolant temperature at the ignition-on state, a temperature difference between the fuel temperature inside the fuel supply line and the intake air temperature at the ignition-on state, and a temperature difference between the coolant temperature and the intake air temperature are less than predetermined values.

It is also preferable that the determining a fuel temperature and a fuel pressure inside a fuel tank comprises: calculating an average fuel pressure of a predetermined number of fuel pressures, detected at predetermined intervals in the fuel supply line; determining whether predetermined conditions for an estimation of a fuel pressure and a fuel temperature inside the fuel tank exist; and setting the fuel temperature inside the fuel supply line as a fuel temperature inside the fuel tank, and setting a pressure difference between the average fuel pressure and a pressure regulator control pressure as the fuel pressure inside the fuel tank, if it is determined that the predetermined conditions for an estimation exist.

It is preferable that if a difference between a current fuel temperature inside the fuel supply line and the fuel temperature inside the fuel supply line at the ignition-on state is not less than a predetermined value, it is determined that the predetermined conditions for an estimation of a fuel pressure and a fuel temperature inside the fuel tank do not exist.

It is further preferable that if a difference between a current fuel temperature inside the fuel supply line and the fuel temperature inside the fuel supply line at the ignition-on state is not less than a predetermined value, a fuel pump speed is not lower than a predetermined speed, or a difference between the calculated average pressure and a calculated average pressure of a previous routine is not less than a predetermined value, it is determined that the predetermined estimation conditions do not exist.

In another preferred embodiment of the present invention, the LPG (Liquefied Petroleum Gas) composition estimation system for an LPI system comprises: a fuel tank, a fuel pump, an injector, a pressure regulator, a detecting unit, and a control unit. In this embodiment, the fuel tank stores LPG fuel. The fuel pump is disposed inside the fuel tank. The fuel pump pressurizes the LPG fuel. The injector is connected to the fuel pump via a fuel supply line. The pressure regulator is disposed in a fuel return line connecting the injector and the fuel tank. The detecting unit detects one or more engine operating parameters and generates corresponding signals. And the control unit receives the signals of the detecting unit and estimates an LPG fuel composition. The control unit being programmed to execute a method comprising: determining whether differences between the detected temperatures fall within predetermined conditions; detecting the fuel temperature and the fuel pressure inside the fuel supply line at intervals; determining a fuel temperature and a fuel pressure inside a fuel tank based on the detected fuel temperature and fuel pressure inside the fuel supply line, if it is determined that the predetermined conditions exist; and determining an LPG fuel composition from saturation vapor pressure data based on the determined fuel temperature and fuel pressure inside the fuel tank.

In a further preferred embodiment of a detecting unit, an ignition detector detects whether a current state is an ignition-on state, an engine-operation state, or an engine-off state. A fuel pressure detector detects a fuel pressure inside a fuel supply line. A fuel temperature detector detects a fuel temperature inside the fuel supply line. A coolant temperature detector detects a temperature of a coolant. An intake air temperature detector detects a temperature of intake air. And a fuel pump speed detector detects a speed of the fuel pump.

An additional preferred embodiment of the method of the present invention includes detecting an LPG temperature and determining whether the LPG temperature has stabilized, detecting an LPG pressure and determining whether an LPG pressure has stabilized, determining an LPG fuel tank temperature based on the detected LPG temperature and determining an LPG fuel tank pressure based on the detected LPG pressure, and estimating and LPG fuel composition based on the LPG fuel tank temperature and the LPG fuel tank pressure.

BRIEF DESCRIPTION OF THE DRAWINGS

The accompanying drawings, which are incorporated in and constitute a part of the specification, illustrate an embodiment of the invention, and, together with the description, serve to explain the principles of the invention, in which:

FIG. 5 shows graphs of the saturation vapor pressure of 100% butane LPG fuel and 70:30 butane/propane ratio LPG fuel.

Like numerals refer to similar elements throughout the several drawings.

DETAILED DESCRIPTION OF THE PREFERRED EMBODIMENTS

Figure 1:
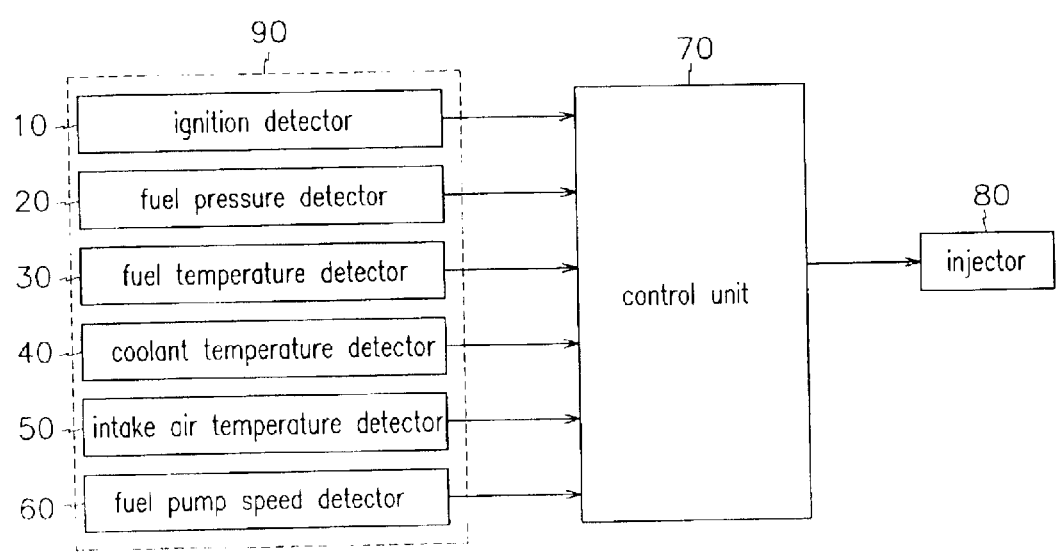
FIG. 1 is a schematic block diagram of an LPG fuel composition estimating system according to a preferred embodiment of the present invention.

As shown in FIG. 1, the LPG fuel composition estimation system according to a preferred embodiment of the present invention includes a detecting unit 90, a control unit 70, and an injector 80. The detecting unit 90, which detects one or more engine operating parameters and generates corresponding signals, includes an ignition detector 10, a fuel pressure detector 20, a fuel temperature detector 30, a coolant temperature detector 40, an intake air temperature detector 50, and a fuel pump speed detector 60.

The control unit 70 preferably includes a processor, a memory, and other necessary hardware and software components as will be understood by persons of ordinary skill in the art to permit the control unit 70 to communicate with sensors and execute the method as described herein. The ignition detector 10 detects operations of an ignition key, that is, it determines whether a current state is an ignition-on state, an engine-operating state, or an engine-off state, and outputs a corresponding signal to the control unit 70. The fuel pressure detector 20 detects the pressure of the LPG fuel in a fuel supply line 106 (FIG. 3), and outputs a corresponding signal to the control unit 70. The fuel temperature detector 30 detects the temperature of the LPG fuel in the fuel supply line 106, and outputs a corresponding signal to the control unit 70. The coolant temperature detector 40 detects the temperature of coolant, and outputs a corresponding signal to the control unit 70. The intake air temperature detector 50 detects the temperature of intake air, and outputs a corresponding signal to the control unit 70. The fuel pump speed detector 60 detects a speed of a fuel pump, which pressurizes the LPG fuel to be delivered to an injector via the fuel supply line 106, and outputs a corresponding signal to the control unit 70.

The control unit 70 receives various signals from the above detectors, and estimates the LPG fuel composition based on the signals. The control unit 70 determines fuel injection timing in consideration of the LPG fuel composition. The fuel injector 80 injects fuel into combustion chambers according to injection command signals input from the control unit 70.

Figure 3:
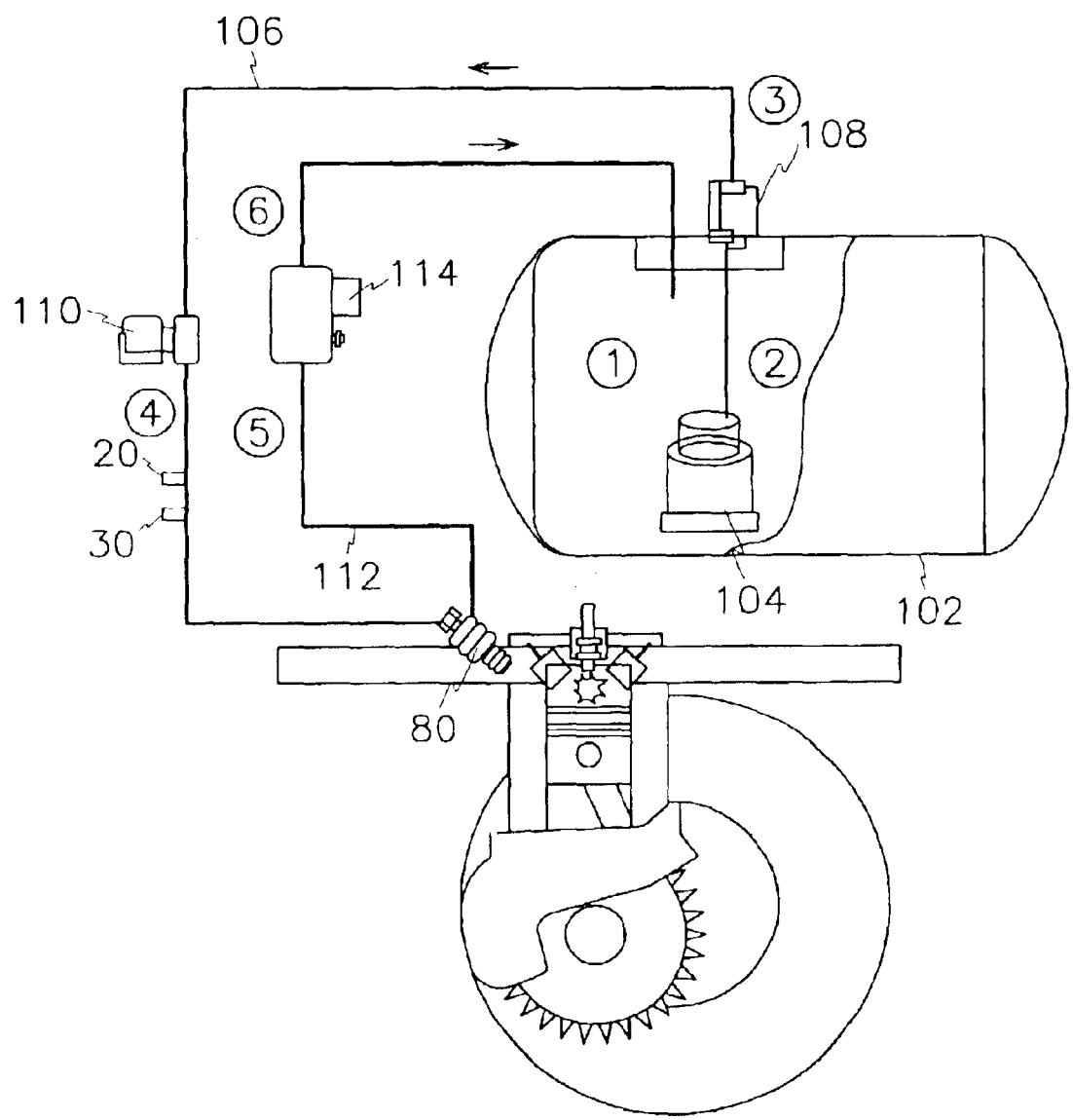
FIG. 3 is a schematic view of an LPG fuel system to which a LPG fuel composition estimating method is applied.

As shown in FIG. 3, the LPG fuel system 100 includes a fuel tank 102, which stores LPG fuel. The LPG fuel is comprised primarily of either butane, propane, or a combination of the two. The LPG fuel inside the fuel tank 102 is maintained in a saturation state, where liquid fuel and gaseous fuel co-exist in an equilibrium state. The LPG fuel inside the fuel tank 102 is pressurized by a fuel pump 104, and is delivered to the injector 80 via the fuel supply line 106. The flow of the LPG fuel inside the fuel supply line 106 is regulated by the operation of a first shut-off valve 108 and a second shut-off valve 110. Conventional solenoid valves can be used for the first shut-off valve 108 and the second shut-off valve 110.

A fuel return line 112 connects the injector 80 and the fuel tank 102, and a pressure regulator 114 is provided in the fuel return line 112. The pressure regulator 114 regulates the pressure of the injector 80 to be higher than the pressure of the fuel tank 102 by a predetermined pressure. The predetermined pressure (hereinafter referred to as the pressure regulator control pressure) is preferably set at 5 bar.

Figure 4:
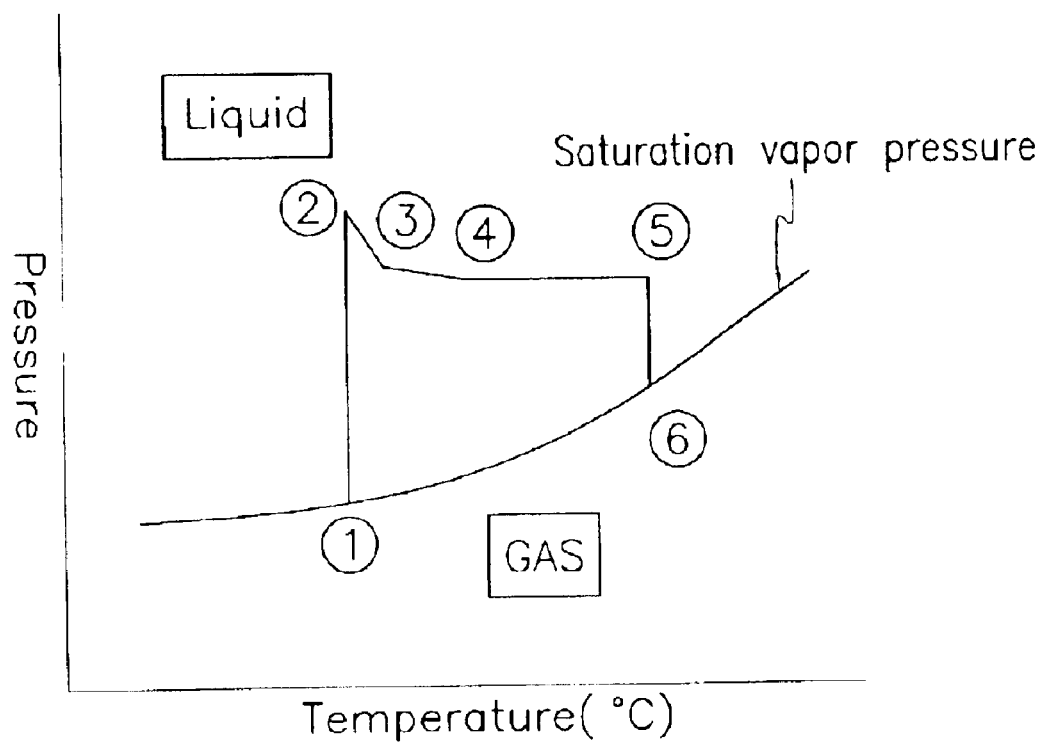
FIG. 4 is a pressure-temperature diagram of LPG fuel in the LPG fuel system of FIG. 3.

As shown in FIG. 4, the LPG fuel inside the fuel tank 102 is in the saturation state 1. The LPG fuel of state 1 changes to state 2 by being pressurized by the fuel pump 104. During this change, the temperature of the LPG fuel is maintained to be substantially constant as the pressure increases. The pressure of LPG fuel pressurized by the fuel pump 104 decreases a small amount while the state of fuel changes from state 2 to state 3, and again from state 3 to state 4. During the change from state 4 to state 5, the pressure of the LPG fuel is substantially maintained, as the pressure regulator 114 maintains the pressure regulator control pressure (for example, 5 bar). The temperature of the fuel changes very little, that is, the temperature in state 1 is substantially equal to the temperature in state 6 (In FIG. 4, the difference in temperature between state 1 and state 6 is shown for the convenience of explanation). For this reason, there is no fuel temperature detector in the fuel return line 112. If a speed of the fuel pump 104 is low, the pressure drop in the fuel return line between the pressure regulator 114 and the fuel tank 102 is very small so that the pressure in state 6 and the pressure in state 1 are approximately equal. States 1–6 are also depicted where they are found in FIG. 3.

In the LPG fuel composition estimation method according to the present invention, the fuel composition is determined based on the temperature and the pressure inside the fuel tank, that is, of state 1. The pressure of state 6 is considered to be the pressure of state 1, and the temperature of state 4, which is detected by the fuel temperature sensor 30, is considered to be the temperature of state 1.

The LPG fuel system, to which the LPG fuel composition estimation method is applied, may vary from the system of FIG. 3 as would be apparent to one of ordinary skill in the art. The LPG fuel composition estimation method according to a preferred embodiment of the present invention will be explained hereinafter with reference to FIG. 2. In step S101, an engine ignition ON demand signal is detected. The control unit 70 detects the fuel pressure P_FUEL_IG and the fuel temperature T_FUEL_IG inside the fuel supply line 106 through the fuel pressure detector 20 and the fuel temperature detector 30, respectively. The control unit 70 also detects the coolant temperature TCO_IG and the intake air temperature TIA_IG through the coolant temperature detector 40 and the intake air temperature detector 50, respectively. In addition, the control unit 70 detects a fuel pressure P_FUEL and a fuel temperature T_FUEL inside the fuel supply line 106, and a coolant temperature TCO and an intake air temperature TIA at predetermined time intervals.

It is then determined whether a relatively long period of time has elapsed after the engine was started, so that temperatures of various areas of the engine are uniform. If so, the procedure of the present invention will be performed, and if not, the procedure ends. The determination of whether temperatures of various areas of the engine are uniform may be performed by comparing the coolant temperature, the intake air temperature, and the fuel temperature inside the fuel supply line 106. In step S102, the control unit 70 calculates a temperature difference ΔT1 between the T_FUEL_IG and the TCO_IG, a temperature difference ΔT2 between the T_FUEL_IG and the TIA_IG, and a temperature difference ΔT3 between the TCO_IG and the TIA_IG. In step S103, the control unit 70 then determines whether the temperature differences ΔT1, ΔT2, and ΔT3 are less than predetermined values.

If so, in step S104, the control unit 70 determines whether the temperature of the fuel supply line has been increased by heat from the engine. In the present invention, the fuel temperature inside the fuel tank is estimated by using the temperature of the fuel supply line. Therefore, if the temperature of the fuel supply line is increased by heat from the engine, the accurate estimation of the fuel temperature inside the fuel tank becomes difficult. Thus, in step S104 the control unit 70 calculates a temperature difference ΔT between a current fuel temperature T_FUEL inside the fuel supply line and the T_FUEL_IG, and determines in step S105 whether the temperature difference ΔT is less than a predetermined value TDEL_FUEL. If so, the control unit 70 determines whether the pressure drop between the pressure regulator 114 and the fuel tank 102 is minimal.

To do this, in step S106 the fuel pump is detected. If the fuel pump 104 operates at high speed, fuel flow is great so that the pressure drop between the pressure regulator 114 and the fuel tank 102 becomes great. Consequently, the estimation of the fuel pressure inside the fuel tank 102 is inaccurate because the fuel pressure inside the fuel return line after the pressure regulator 114 is used to estimate the fuel pressure inside the fuel tank 102. Therefore, it is preferable that the estimation is performed during a minimal fuel flow. A fuel pump generally used for the LPG fuel system has several steps of rotational speed. If such fuel pump is used, pressures estimation should be performed with the fuel pump operating at the lowest speed, which is the first speed.

In step S107, the control unit 70 determines whether the fuel pump operates at the first speed. Preferably, the first speed of the fuel pump is set at 500 rpm.

On the other hand, if the speed of the fuel pump does not have several steps but changes continuously within a range, the determination of whether the pressure drop is less than the predetermined value may be performed by determining whether the speed of the fuel pump is less than a predetermined speed.

Figure 2:
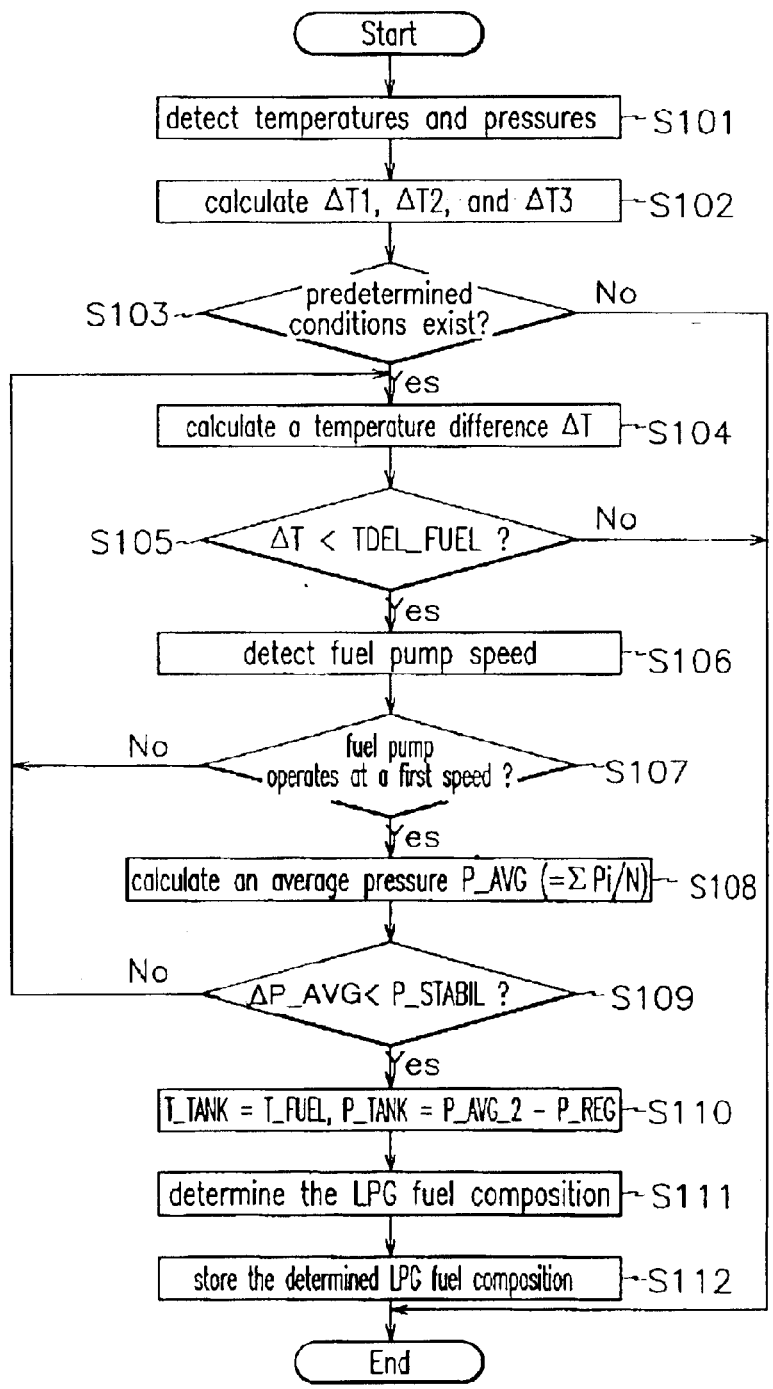
FIG. 2 is a flowchart of an LPG fuel composition estimating method according to a preferred embodiment of the present invention.

If it is determined that the fuel pump operates at the first speed in step S107, it is determined whether the fuel pressure is stable based on the average fuel pressure. To determine whether the fuel pressure is stable, the fuel pressure inside the fuel supply line is detected a predetermined number of times N at predetermined intervals. In step S108, the control unit 70 calculates an average pressure P_AVG (=Pi/N). Then, in step S109, the control unit 70 then determines whether an average pressure difference ΔP_AVG between the current average pressure P_AVG_2 and the previous average pressure P_AVG_1 is less than a predetermined value P_STABIL. The procedure of FIG. 2 is repeatedly performed, and the average pressure is stored in a memory to which the control unit 70 has access. The previous average pressure P_AVG_1 is the value P_AVG stored from the previous repetition.

If it is determined that the average pressure difference ΔP_AVG is less than the predetermined value P_STABIL in step S109, in step S110 the control unit 70 sets the fuel temperature T_FUEL inside the fuel supply line as the fuel temperature T_TANK inside the fuel tank, and sets the difference between the current average pressure P_AVG_2 and the control pressure P_REG of the pressure regulator as the fuel pressure P_TANK in the fuel tank. In step S111, the control unit 70 then determines the LPG fuel composition (a butane/propane ratio of the LPG fuel) from a saturation vapor pressure lookup table based on the T_TANK and the P_TANK values. The saturation vapor pressure lookup table includes LPG fuel compositions under specific fuel temperatures and pressures. Such a lookup table is easily determined through experiments by a person of ordinary skill in the art. The control unit 70 stores the determined LPG fuel composition in a memory in step S112, and the procedure ends.

Using the determined LPG composition, the amount of fuel liquification may be determined, and thereby an optimal fuel injection timing may be determined. It is preferable that a butane ratio is reset at 100% if a battery reset occurs.

As stated above, the LPG fuel composition estimation method according to a preferred embodiment of the present invention determines the fuel temperature and pressure inside the fuel tank after the termination of engine warm-up after the ignition is turned on, and estimates the LPG composition using the determined fuel temperature and pressure. From the estimated LPG fuel composition, a precise fuel injection timing may be determined so the stability of the engine increases, and emissions may be improved.

Although preferred embodiments of the present invention have been described in detail hereinabove, it should be clearly understood that many variations and/or modifications of the basic inventive concepts herein taught which may appear to those skilled in the present art will still fall within the sprit and scope of the present invention, as defined in the appended claims.

What is claimed is:

1. A liquefied petroleum gas (LPG) fuel composition estimation method for an LPG injection (LPI) system, comprising:
   detecting a fuel pressure inside a fuel supply line, a fuel temperature inside the fuel supply line, a coolant temperature, and an intake air temperature at an ignition-on state;
   determining whether predetermined conditions exist between the detected temperatures;
   detecting the fuel temperature and the fuel pressure inside the fuel supply line at predetermined intervals;
   determining a fuel temperature and a fuel pressure inside a fuel tank based on the detected fuel temperature and fuel pressure inside the fuel supply line, if it is determined that the predetermined conditions exist; and
   determining an LPG fuel composition from saturation vapor pressure data based on the determined fuel temperature and fuel pressure inside the fuel tank.

2. The LPG composition estimation method of claim 1, wherein the predetermined conditions comprise:
   a first temperature difference between the fuel temperature inside the fuel supply line and the coolant temperature at the ignition-on state is less than a first predetermined value; a second temperature difference between the fuel temperature inside the fuel supply line and the intake air temperature at the ignition-on state is less than a second predetermined value; and
   a third temperature difference between the coolant temperature and the intake air temperature is less than a third predetermined value.

3. The LPG composition estimation method of claim 1, wherein the determining a fuel temperature and a fuel pressure inside a fuel tank comprises:
   calculating an average fuel pressure of a predetermined number of detected fuel pressures in the fuel supply line;
   determining whether predetermined estimation conditions exist for an estimation of a fuel pressure and a fuel temperature inside the fuel tank; and
   setting the fuel temperature inside the fuel tank as the fuel temperature inside the fuel supply line, and setting the fuel pressure inside the fuel tank as a pressure difference between the average fuel pressure and a pressure regulator control pressure, if it is determined that the predetermined estimation conditions exist.

4. The LPG fuel composition estimation method of claim 3, wherein if a difference between a current fuel temperature inside the fuel supply line and the fuel temperature inside the fuel supply line at the ignition-on state is not less than a predetermined value, it is determined that the predetermined estimation conditions do not exist.

5. The LPG fuel composition estimation method of claim 3, wherein if a difference between a current fuel temperature inside the fuel supply line and the fuel temperature inside the fuel supply line at the ignition-on state is not less than a predetermined value, a fuel pump speed is not lower than a predetermined speed, or a difference between the calculated average pressure and a calculated average pressure from a previous routine is not less than a predetermined average pressure value, it is determined that the predetermined estimation conditions do not exist.

6. An LPG composition estimation system for an LPI system, comprising:
   a fuel tank for storing LPG fuel;
   a fuel pump disposed inside the fuel tank, the fuel pump pressurizing the LPG fuel;
   an injector connected to the fuel pump via a fuel supply line;
   a pressure regulator disposed in a fuel return line connecting the injector and the fuel tank;
   a detecting unit for detecting one or more engine operating parameters and generating corresponding signals; and
   a control unit receiving the signals of the detecting unit and estimating an LPG fuel composition, the control unit being programmed to execute a method comprising:
   detecting a fuel pressure inside a fuel supply line, a fuel temperature inside the fuel supply line, a coolant temperature, and an intake air temperature at an ignition-on state;
   determining whether predetermined conditions fall within differences between the detected temperatures;
   detecting the fuel temperature and the fuel pressure inside the fuel supply line at intervals;
   determining a fuel temperature and a fuel pressure inside a fuel tank based on the detected fuel temperature and fuel pressure inside the fuel supply line; and
   determining an LPG fuel composition from saturation vapor pressure data based on the determined fuel temperature and fuel pressure inside the fuel tank.

7. The LPG composition estimation system of claim 6, wherein the detecting unit comprises:
   an ignition detector detecting whether a current state is an ignition-on state, an engine-operating state, or an engine-off state;
   a fuel pressure detector for detecting a fuel pressure inside a fuel supply line;
   a fuel temperature detector for detecting a fuel temperature inside the fuel supply line;
   a coolant temperature detector for detecting a temperature of coolant;
   an intake air temperature detector for detecting a temperature of intake air; and
   a fuel pump speed detector for detecting a speed of the fuel pump.

8. The LPG fuel composition estimation system of claim 6, wherein the predetermined conditions comprise:
   a first temperature difference between the fuel temperature inside the fuel supply line and the coolant temperature at the ignition-on state is less than a first predetermined value; a second temperature difference between the fuel temperature inside the fuel supply line and the intake air temperature at the ignition-on state is less than a second predetermined value; and a third temperature difference between the coolant temperature and the intake air temperature is less than a third predetermined value.

9. The LPG fuel composition estimation system of claim 6, wherein the determining a fuel temperature and a fuel pressure inside a fuel tank comprises:

calculating an average fuel pressure of a predetermined number of detected fuel pressures in the fuel supply line;

determining whether predetermined estimation conditions exist for an estimation of a fuel pressure and a fuel temperature inside the fuel tank; and setting the fuel temperature inside the fuel tank as the fuel temperature inside the fuel supply line, and setting the fuel pressure inside the fuel tank as a pressure difference between the average fuel pressure and a pressure regulator control pressure, if it is determined that the predetermined estimation conditions exist.

10. The LPG fuel composition estimation system of claim 9, wherein if a difference between a current fuel temperature inside the fuel supply line and the fuel temperature inside the fuel supply line at the ignition-on state is not less than a predetermined value, it is determined that the predetermined estimation conditions do not exist.

11. The LPG fuel composition estimation system of claim 9, wherein if a difference between a current fuel temperature inside the fuel supply line and the fuel temperature inside the fuel supply line at the ignition-on state is not less than a predetermined value, a fuel pump speed is not lower than a predetermined speed, or a difference between the calculated average pressure and a calculated average pressure from a previous routine is not less than a predetermined average pressure value, it is determined that the predetermined estimation conditions do not exist.

* * * * *